United States Patent
Ryan

(10) Patent No.: US 7,618,821 B2
(45) Date of Patent: Nov. 17, 2009

(54) SIMULATED BLOOD COMPONENTS AND METHODS

(75) Inventor: Wayne L. Ryan, Omaha, NE (US)

(73) Assignee: Streck, Inc., LaVista, NE (US)

( * ) Notice: Subject to any disclaimer, the term of this patent is extended or adjusted under 35 U.S.C. 154(b) by 0 days.

(21) Appl. No.: 12/100,658

(22) Filed: Apr. 10, 2008

(65) Prior Publication Data

US 2008/0254543 A1 Oct. 16, 2008

Related U.S. Application Data

(60) Provisional application No. 60/911,567, filed on Apr. 13, 2007, provisional application No. 60/911,610, filed on Apr. 13, 2007.

(51) Int. Cl.
*G01N 31/00* (2006.01)
*G01N 33/48* (2006.01)

(52) U.S. Cl. .............. 436/10; 436/8; 436/17; 436/18; 436/63; 436/150; 436/164; 436/166; 436/174; 435/2; 422/73

(58) Field of Classification Search ............ 436/8, 436/10, 16, 17, 18, 63, 149, 150, 164, 166, 436/174, 175; 435/2, 29; 422/73, 82.01, 422/82.05

See application file for complete search history.

(56) References Cited

U.S. PATENT DOCUMENTS

| | | | |
|---|---|---|---|
| 3,873,467 A | 3/1975 | Hunt | |
| 4,436,821 A * | 3/1984 | Ryan | 436/10 |
| 5,196,182 A | 3/1993 | Ryan | |
| 5,262,327 A | 11/1993 | Ryan | |
| 5,270,208 A | 12/1993 | Ryan | |
| 5,320,964 A | 6/1994 | Young et al. | |
| 5,432,089 A | 7/1995 | Ryan et al. | |
| 5,460,797 A | 10/1995 | Ryan | |
| 5,529,933 A | 6/1996 | Young et al. | |
| 5,811,099 A | 9/1998 | Ryan | |
| 5,849,517 A | 12/1998 | Ryan | |
| 5,858,790 A | 1/1999 | Kim et al. | |
| 5,874,310 A | 2/1999 | Li et al. | |
| 5,874,311 A | 2/1999 | Li et al. | |
| 5,917,584 A | 6/1999 | Li et al. | |
| 6,060,322 A | 5/2000 | Horton et al. | |
| 6,187,590 B1 | 2/2001 | Kim et al. | |
| 6,200,500 B1 | 3/2001 | Ryan | |
| 6,221,668 B1 | 4/2001 | Ryan et al. | |
| 6,228,652 B1 | 5/2001 | Rodriguez et al. | |
| 6,232,125 B1 | 5/2001 | Deka et al. | |
| 6,362,003 B1 | 3/2002 | Young et al. | |
| 6,399,388 B1 * | 6/2002 | Ryan et al. | 436/8 |
| 6,403,377 B1 * | 6/2002 | Ryan et al. | 436/8 |
| 6,406,915 B2 * | 6/2002 | Ryan et al. | 436/10 |
| 6,448,085 B1 * | 9/2002 | Wang et al. | 436/10 |
| 6,653,137 B2 | 11/2003 | Ryan | |
| 6,723,563 B2 | 4/2004 | Ryan | |
| 6,962,817 B2 | 11/2005 | Li et al. | |
| 7,109,036 B2 | 9/2006 | Ortiz et al. | |
| 7,135,341 B2 | 11/2006 | Ortiz et al. | |
| 7,195,919 B2 | 3/2007 | Jacobs et al. | |
| 7,198,953 B2 | 4/2007 | Ortiz et al. | |
| 7,285,417 B2 * | 10/2007 | Ortiz et al. | 436/10 |
| 7,354,767 B2 * | 4/2008 | Ortiz et al. | 436/10 |
| 2005/0079623 A1 * | 4/2005 | Ortiz et al. | 436/63 |
| 2005/0227359 A1 | 10/2005 | Ortiz et al. | |

FOREIGN PATENT DOCUMENTS

WO 2004/003568 A 1/2004

OTHER PUBLICATIONS

European Search Report, Application No. 08007208.5, Dated Aug. 21, 2008.
Ruzicka, "The New Hematology Analyzer Sysmex XE-2100," vol. 125, Mar. 2001, pp. 91-96.

* cited by examiner

*Primary Examiner*—Maureen M Wallenhorst
(74) *Attorney, Agent, or Firm*—Dobrusin & Thennisch PC

(57) ABSTRACT

A control and a cellular fraction for use therein and methods for making the same, including a first cellular component including a plurality of a first group of processed animal red blood cells other than human blood cells; a second cellular component including a plurality of a second group of processed animal red blood cells other than human blood cells; a third cellular component including a plurality of a third group of processed animal red blood cells other than human blood cells; wherein one or more of the first second and third cellular components include a nucleus; and the control simulates erythroblasts of a human blood sample on an automated blood analyzer that analyzes blood cells using impedance, optical measurements or both.

26 Claims, No Drawings

SIMULATED BLOOD COMPONENTS AND METHODS

CLAIM OF BENEFIT OF FILING DATE

The present application claims the benefit of the filing date of U.S. Provisional Application Ser. No. 60/911,567 (Filed Apr. 13, 2007) and U.S. Provisional Application Ser. No. 60/911,610 (Filed Apr. 13, 2007), and the entirety of the contents of these applications being hereby expressly incorporated by reference.

FIELD OF THE INVENTION

This invention relates to simulated blood components and more particularly to simulated blood components for use in controls for automated hematology analyzers.

BACKGROUND OF THE INVENTION

A popular tool for the analysis of blood is an automated hematology analyzer. In general, such instruments use particle detection technologies to identify the existence of one or more components of whole blood. Such detection technologies may include, for example, particle light scatter detection, particle impedance as measured by DC current, RF frequency, or otherwise. A number of patent documents address controls for use in an automated hematology analyzer COULTER® GEN-S™ Hematology Analyzer or the COULTER® LH series analyzer, available from Beckman Coulter Corp., the ADVIA® 2120 Hematology System from Bayer, the CELL-DYN 4000 from Abbott, and the Sysmex XE-2100™ Automated Hematology Analyzer from Sysmex, or the like for simulating the characteristics of one or more of detectable characteristics of blood cell components. One particular component that has received attention has been nucleated red blood cells, also known as erythroblasts. See, generally, U.S. Pat. Nos. 7,135,341; 6,962,817; 6,723,563; 6,653,137; 6,221,668; 6,200,500; 6,187,590; and 5,858,790; all incorporated by reference herein. Notwithstanding the above, there remains a need for controls and specifically cellular components for simulating erythroblasts.

The present invention addresses one or more of the above needs by providing improved controls and their cellular fractions, and methods for making controls and a cellular fraction for the controls.

SUMMARY OF THE INVENTION

By way of summary, the present invention meets some or all of the above needs by providing in a first aspect a cellular fraction for a stand-alone erythroblast control, comprising: a first cellular component including a plurality of a first group of processed animal red blood cells other than human blood cells; a second cellular component including a plurality of a second group of processed animal red blood cells other than human blood cells; and a third cellular component including a plurality of a third group of processed animal red blood cells other than human blood cells; wherein one or more of the first, second and third cellular components include a nucleus; and at least a portion of the cellular fraction functions to simulate erythroblasts of a human blood sample on an automated blood analyzer that analyzes blood cells using impedance, optical measurements or both.

The present invention also meets some or all of the above needs by providing in a first aspect cellular fraction for a stand-alone erythroblast control, consisting essentially of a lysable cellular cell component for simulating human red blood cells; a first cellular component including a plurality of a first group of processed animal red blood cells other than human blood cells; a second cellular component including a plurality of a second group of processed animal red blood cells other than human blood cells; and a third cellular component including a plurality of a third group of processed animal red blood cells other than human blood cells; wherein one or more of the first, second and third cellular components include a nucleus; and at least a portion of the cellular fraction functions to simulate erythroblasts of a human blood sample on an automated blood analyzer that analyzes blood cells using impedance, optical measurements or both.

The first or second aspect may be characterized by one or any combination of the following features: one or more of the first, second or third cellular components is a processed red blood cell derived from alligators, turkeys, geese, chickens, sharks, cows, pigs, goats, salmon, trout, or another source of a blood cell with a nucleus; cells from the third cellular component of the cellular fraction function to simulate erythroblasts of a human blood sample on an automated blood analyzer that analyzes blood cells using impedance, optical measurements or both; upon passing through an automated hematology analyzer cells of the first and second cellular components are detected by the analyzer as a white blood cell, and cells of the third cellular component are detected as an erythroblast; the cells of the first and second cellular components, upon analysis of the cells by the analyzer fail to provide a white blood cell differentiation within ranges consistent with human whole blood; at least one of the first, second or third cellular components has a size less than about 450 fL; or at least one of the first, second or third cellular components is a processed red blood cell derived from alligators.

A third aspect of the invention also meets some or all of the above needs, by providing a cellular fraction for a blood cell control, comprising: a first part that includes a plurality of cellular components; and a second part that includes at least one cellular component including a plurality of alligator red blood cells processed for simulating erythroblasts of a human blood sample on an automated blood analyzer; wherein upon passing through an automated hematology analyzer the cellular components of the first part are detected by the analyzer as a white blood cell, and the second part is detected as an erythroblast.

The third aspect of the invention may be further characterized by one or any combination of the following features: the cellular component of the second part includes red blood cells derived from an alligator; the cellular components of the first part, upon analysis by the analyzer fail to provide a white blood cell differentiation within ranges consistent with human whole blood; or at least a portion of the second part functions o simulate erythroblasts of a human blood sample on an automated blood analyzer that analyzes blood cells using impedance, optical measurements or both.

A fourth aspect of the invention also meets some or all of the above needs, by providing a method of making a control for resembling an erythroblast population, comprising the steps of admixing in an aqueous diluent: a first cellular component including a plurality of a first group of processed animal red blood cells other than human blood cells; a second cellular component including a plurality of a second group of processed animal red blood cells other than human blood cells; and a third cellular component including a plurality of a third group of processed animal red blood cells other than human blood cells; wherein one or more of the first second and third cellular components include a nucleus; and the resulting control simulates erythroblasts of a human blood sample on an automated blood analyzer that analyzes blood cells using impedance, optical measurements or both. The fourth aspect also contemplates a control prepared according to such method.

The present invention provides a quality control composition for use in automated hematology analyzers, and particularly a cellular fraction (including its respective cellular components or parts) that is employed in the control. The control composition and the cellular fraction comprise components for simulating erythroblasts, useful in a hematology analyzer to detect the presence of erythroblasts in a blood sample. Products herein exhibit excellent shelf-life and stability and maintain their integrity under analysis conditions. The components of the cellular fraction of the control composition are not necessarily structurally and chemically similar to the corresponding human blood cells. On the contrary, the makeup of the cellular components may differ greatly from that of the human blood cell it is designed to emulate. However, generally, the control composition (and specifically its cellular fraction) will have detectable characteristics (e.g., physical characteristics) that simulate such characteristics of whole blood. Thus, the control and its cellular fraction will exhibit a predictable response when analyzed by a detection method, substantially mimicking the response of human blood cells under the same detection method.

DETAILED DESCRIPTION

The present invention is predicated upon a unique combination of cellular components in a cellular fraction, which is able to simulate a population of erythroblasts when passed through an automated hematology analyzer adapted for detecting erythroblasts. The combination makes the overall composition attractive for use as a "stand-alone" control, i.e., a control that functions to mimic erythroblasts, but not necessarily for use to differentiate sub-populations of white blood cells. Thus, in one aspect, the invention is directed to a stand-alone erythroblast control; that is, a control intended for simulating a population of erythroblasts, and more particularly a control having its primary, if not sole function as simulating an erythroblast population. Of course, it will be appreciated that the compositions herein can be modified in accordance with art-disclosed teachings to arrive at a control that functions to simulate an erythroblast population and one or more other populations normally encountered in whole blood (e.g. human whole blood). For instance, one possible approach contemplates a control that simulates detectable characteristics of an erythroblast population plus one or a combination of platelets, reticulated platelets, white blood cells (including one, two, three, four or five white blood cell populations), reticulocytes, immature granulocytes (e.g., per U.S. Pat. No. 7,109,036, incorporated by reference), or any combination thereof. Thus, without limitation, the controls of the present invention may be employed in combination (e.g. as a mixture, a kit comprising discrete individual controls, or both) with a control as disclosed in U.S. Pat. Nos. 6,723,563; 6,653,137; 6,221,668; or 6,200,500, all incorporated by reference. It will be appreciated that one or more of the simulated blood cell components in the controls herein may include a synthetic particle (e.g., a synthetic polymer, such as polystyrene), as discussed in U.S. Pat. No. 6,962,817, incorporated by reference.

It is envisioned that a control herein may particularly include a lysable red blood cell component, such as a cell prepared according to the teachings of U.S. Pat. Nos. 6,200, 500 and 6,221,668, incorporated by reference.

In general, the control compositions herein exhibit long term stability, and particularly stability that substantially exceeds the stability of a fresh whole blood (e.g. human blood) sample containing fresh erythroblasts (e.g. human erythroblasts). For example, the controls, their respective cellular fractions, or both, have a useful life of at least 10 days from manufacture date, and more specifically at least 1 month, 2 months or even 6 months from manufacture date.

In one specific aspect, the controls herein comprise a suspended cellular fraction that includes at least one population of processed animal red blood cells for specifically simulating erythroblasts.

In another specific aspect of the invention, it is contemplated that the suspended cellular fraction in the reference control comprises a plurality of subgroups of human or animal red or white blood cells that have each been processed independent of the other according to individual processing parameters, before being combined in a common suspension liquid. For instance, in one approach the suspended particles include at least two, at least three, at least four, or even at least five individually processed subgroups of animal red blood cells. The processing of animal red blood cells to simulate erythroblasts has been addressed throughout the art. See e.g. U.S. Pat. Nos. 7,135,341; 6,723,563; 6,187,590; and 5,858, 790, all incorporated by reference. Examples of suitable blood cell sources include, without limitation, humans, mammals, birds, reptiles, and fish. Specific cell sources are alligators, turkeys, geese, chickens, sharks, cows, pigs, goats, salmon, trout, or another source of a blood cell with a nucleus.

According to the teachings herein, when a plurality of subgroups of animal red blood cells is used, the starting blood cells may be cells from the same type of animal, or from different types of animals. For example, each of two, three, four, or five subgroups may be cells from a reptile, or they may be cells from a reptile and a bird, a bird and fish, a mammal, bird, fish and reptile. Most preferably, the source of blood is alligator blood, turkey blood or a mixture thereof. Desirably the blood is selected from a source from which cells useful for preparing the control will have a nucleus, and also have a mean cell volume in its initial as-provided state in the range of about 160 to about 330 fl, more preferably about 190 fl to 310 fl, and still more preferably, a mean cell volume range from 230 fl to 290 fl.

More specifically, according to the teachings herein, when a plurality of subgroups of animal red blood cells is used, the starting blood cells may be cells from the same type of animal, or from different types of animals. Two or more of the cells may be prepared according to a different set of process conditions. For example, each of two, three, four, or five subgroups may be cells from a reptile, or they may be cells from a reptile and a bird, a bird and fish, a mammal, bird, fish and reptile. Of course it is also possible to employ human blood cells that have been processed for realizing long term stability. It is possible herein that an erthyroblast cell population may be simulated based upon processing of a single blood cell. One specific preferred embodiment for providing a stand-alone control includes a cellular fraction that includes a plurality of different types of blood cells, (e.g., a first turkey cell processed according to a first set of conditions, and a second turkey cell processed according to a second set of conditions different from the first set of conditions, and a processed alligator cell; one or more processed shark cells and one or more processed alligator cell; a processed turkey cell, a first processed alligator cell, and a second processed alligator cell that is processed in a manner different than the first processed alligator cell; any combination of the foregoing, or otherwise).

In general, the starting cells are received from the blood source and are washed and separated from the remainder of the blood components. For example, the cell source blood is received as whole blood that has been contacted with a first suitable suspension solution, e.g. an Alsever's solution, Hank's solution or otherwise. The cells are typically washed with a second suitable solution (e.g., an isotonic wash solution that is the same as or different from the first suitable suspension solution), before, during, and/or after (or any combination thereof a separation step, such as a step of separation by a separation technique such as filtration, centrifugation, sedimentation, or any combination thereof. In general, a single blood cell population (e.g. animal red blood cells from human white blood cells or another blood cell population) is separated from the remainder of the blood is achieved. The separated cells may then be resuspended in a third suitable suspension solution (the same as or different from the first and/or second suspension solutions). It is possible that the suspension solution, the isotonic wash solution or both may include distilled and/or de-ionized water; and one or more of a fungicide of up to about 5 parts; an antimicrobial of up to about 5 parts; a surfactant ranging from about 5 parts to about 20 parts; a buffer ranging from about 5 parts to about 30 parts, a metal chelating agent ranging from about 25 parts to 50 parts; a cell nutrient of up to about 5 parts; and an agent for maintaining tonicity in about 15 parts to about 35 parts; or any combination thereof.

The isotonic solution may also contain other ingredients as described in U.S. Pat. Nos. 5,858,790 or 6,187,590 (incorporated by reference herein). Optionally, though certain of the above may already perform such functions, the solution may also include one or more agents that function as a hemolysis inhibitor, an aggregating agent, cell size, shape or volume stabilizer, metabolite, protein source, an agent for properly positioning the white blood cell subpopulation (e.g., a lipoprotein), an antioxidant, a debris reducer or a mixture thereof.

Once separated, the cells to be employed in the control are processed for realizing a subgroup of cells that are generally similar to each other (e.g. generally monodisperse) in terms of diameter, volume, electrical characteristics, light scatter characteristics, any combination thereof or other characteristic detectable by the automated instrument. As indicated, more than one distinct subgroup of cells may be prepared, each one processed according to specific individual process.

The cells may be processed for preserving their size, content or both; for preserving one or more antigens on a cell surface, or any combination During the cell processing step, typically one or more techniques are performed for: increasing cell volume; decreasing cell volume; removing hemoglobin; removing cytoplasm; cross-linking a membrane; cross-linking a cell content; denaturing cell content; denaturing a membrane; removing a membrane; repairing a membrane; introducing a substance within a membrane; or any combination thereof. For example, one approach is to employ a process including or consisting essentially of steps of increasing cell volume; and cross-linking or otherwise denaturing a cell membrane.

Any of a number of art-disclosed techniques may be employed, such as those described in U.S. Pat. Nos. 7,135,341; 6,723,563; 6,653,137; 6,221,668; 6,200,500; 6,187,590; and 5,858,790; all incorporated by reference herein. Among the techniques, for example, are thermal processing, chemical processing, or both. Chemical processing involves processing with a chemical for achieving a chemical reaction on or within a cell, a physical modification of the cell or its contents, or any combination thereof. Multiple techniques may be performed simultaneously or sequentially upon a particular cell. Preferably the solution will include at least one or more, more preferably two or more, still more preferably three or more, still more preferably four or more and still even more preferably all of the following ingredients: a fungicide; an antimicrobial; a surfactant; a buffer; a metal chelating agent; a cell nutrient; or an agent for maintaining tonicity.

It is possible that cells may be subjected to one or more processing steps, each for realizing a separate result. For example, a cell may be swollen or shrunk, and then fixed. A cell may be swollen or shrunk, and hemoglobin removed, and then fixed. A cell may be swollen or shrunk, RNA introduced to the cell and then fixed. A cell may have a membrane removed and the nucleus fixed. A cell may simply be fixed. A cell may be swollen or shrunk and then remain unfixed. A cell may be contacted with a lipoprotein (e.g. as taught in U.S. Pat. Nos. 5,270,208; 5,262,327; and 6,723,563, incorporated by reference). It will be appreciated that even though the teachings herein are specifically exemplified by reference to particular NRBC controls, they are not intended to be so limited. Various of the techniques herein may be employed for preparing controls for simulating other blood cell components. For example, it is contemplated that the teachings herein can be employed for preparing one or more blood cell components for simulating one or more subpopulations of white blood cells.

In the past, the use of hypotonic solutions to swell cells has been employed. See, U.S. Pat. No. 5,320,964. According to one aspect of the invention, it is possible to be free of any such step of employing a hypotonic solution. It is contemplated, for instance, that cells from a blood source can be contacted with a hypertonic solution for causing a change in cell size. An animal red blood cell thus can be processed by contacting with a hypertonic solution of sufficient concentration and at a suitable temperature for changing the cell size to approximate the size of a cell from one or more of the five white blood cell subpopulations (a lymphocyte, a monocyte, an eosinophil, a basophill, a neutrophil). Examples of hypertonic solutions could include, without limitation, solutions of one or more of a salt or a sugar. By way of more specific examples, the solution may be a metal halide solution (e.g., one or more chlorides, bromides, or iodides of one or more of sodium, magnesium, calcium, or potassium), any combination thereof, or the like); polyols (e.g., ethylene glycol, propylene glycol, glycerol), alkyl sulfoxides (e.g., dimethyl sulfoxide), alkyl formamides (e.g., dimethylformamide), alkyl acetamides (e.g., dimethylacetamide), a urea, or any combination thereof. The hypertonic solution may be an aprotic solvent, e.g., a dipolar aprotic solvent. The hypertonic solution generally will have an osomolarity greater than about 300 mosmol, more specifically greater than 330 mOsm, still more specifically greater than 370 mOsm, and still more specifically greater than 410 mOsm (e.g., about 430 to 450 mOsm). In one embodiment, the hypertonic solution is generally an acidic solution, although it may also be basic or neutral.

When employed for changing cell size, the process herein can be employed for altering the volume relative to the original cell volume by as much as 70% or greater. Ordinarily however, volume change will be less than 50%, or even less than 30% (e.g. as low as about 10% or even 20%).

In the context of the stand-alone controls herein, as mentioned, it is possible that the control will not only function to simulate human erythroblasts, but may also function to simulate one or more subpopulations of human white blood cells for allowing differentiation of the individual subpopulation. In another respect, the control, its cellular fraction, or both, include a component for simulating human erythroblasts, along with a component for causing the analyzer to provide a white blood cell population count, but not differentiate white blood cell subpopulations according to their normal levels. Thus, a control herein may include a function in accordance with U.S. Pat. No. 3,873,467 (Hunt) incorporated by reference. Thus, methods herein contemplate detecting and counting of simulated erythroblasts and detecting and counting of simulated white blood cells, with or without white blood cell subpopulation differentiation.

As gleaned from the above, in general, the controls of the present invention will include a particulated phase, and specifically a blood cell fraction (e.g., one containing two or more different cellular components), suspended in liquid medium. It is contemplated that the cell fraction may include cellular components that are detectable by an analyzer as an erythroblast, or as a combination of erythroblasts and white blood cells. The cell fraction concentration will generally be within or be adaptable to be diluted or concentrated within an instrument, to fall within one or more pre-selected and reproducible ranges, e.g., for simulating levels that would reproducibly correspond with normal levels of erythroblasts, or predetermined abnormal levels of erythroblasts. For example, the cells provided for simulating erythroblasts might be employed in an amount corresponding to about 1 to about 15% of the total cells that would be counted by an analyzer (e.g., one control might have a lower level of erythroblasts, such as about 2 to 8% of the total cells that would be counted by an analyzer as a white blood cell; another control might have a higher level of erythroblasts, such as about 8% to 12% of the total cells that would be counted by an analyzer as a white blood cell). More particularly, a first control might employ cells in the amounts of about 2 to 4 million lysable red blood cells/ul (e.g., about 3 million), about 1,600 to 2,400 cells/ul (e.g., about 2000 cells/ul) that would be counted by an analyzer as a white blood cell, and about 40 to 160 cells/ul that would be counted by the analyzer as erythroblasts. A second control might employ cells in the amounts of about 2 to 4 million lysable red blood cells/ul (e.g., about 3 million), about 1,600 to 2,400 cells/ul (e.g., about 2000 cells/ul) that would be counted by an analyzer as a white blood cell, and greater than about 160 cells/ul to 240 cells/ul that would be counted by the analyzer as erythroblasts. The first control and the second control can be packaged as a kit, alone or with another control. The above cell amounts are exemplary and may be varied.

The viscosity of any liquid medium employed (e.g., as a suspension medium for the cellular fraction) likewise typically will resemble or will be processed (e.g., by one or more steps of diluting or thickening the medium) so that the resulting material resembles that of blood as it is encountered in normal hematology analyzer instrument operation. Many different solutions are available for use in or as the liquid suspension medium or otherwise as a solution for processing cells according to the present invention. By way of example, without limitation, the liquid medium may include or consist essentially of a composition selected from one or any combination of the compositions of Disodium EDTA, Magnesium Gluconate, $Na_2HPO_4$, PEG 20,000, Inosine, Glucose, Na Fluoride, NaOH, BSA, Sulfasalazine, Methyl Paraben, Neomycin Sulfate or Chloramphenicol. Examples of suitable media may also be gleaned from one or more of U.S. Pat. Nos. 7,135,341; 6,723,563; 6,653,137; 6,221,668; 6,200,500; 6,187,590; and 5,858,790; all incorporated by reference herein.

Without limitation, examples of various media are also provided in the Following Table 1 and Table 2, illustrating examples of compositional ranges for the solutions useful herein. The ultimate desired concentrations may be varied as desired to take into account the particular materials and processing conditions selected by the user. For example, one approach may be to select a concentration (in mg %) that falls toward the central portion of the stated ranges of Table 1, and with reasonable experimentation select the ultimate optimal concentration for the specific application. In addition to the following it is possible that a phosphate buffered solution (which may itself include one or more other ingredients, such as a surfactant (e.g., a suitable concentration of a cationic, anionic, or even a nonionic surfactant, like 1% w/v Triton X). Hank's solution, or a composition including the same may also be employed.

TABLE 1

| Chemical | A (mg %) | B (mg %) | C (mg %) | D (mg %) | E (mg %) | F (mg %) |
|---|---|---|---|---|---|---|
| EDTA (NA2) | 1500-1820 | 1100-1250 | 1100-1250 | 600-800 | 600-800 | 90-110 |
| Mg Gluconate | 880-980 | 600-700 | 600-700 | 360-420 | 360-420 | — |
| NA2HPO4 | 600-680 | 400-500 | 400-500 | 240-300 | 240-300 | 60-80 |
| PEG-20k | 550-850 | 550-850 | 550-850 | 550-850 | 550-850 | 850-1100 |
| Inosine | 20-30 | 20-30 | 20-30 | 10-30 | 80-120 | — |
| Glucose | — | 1000 | 800-1200 | 500-700 | 500-700 | — |
| NaF | — | 3-7 | 3-7 | — | — | — |
| NaOH | 180-225 | 120-160 | 120-160 | 75-85 | 75-95 | — |
| BSA | — | — | 2000 | — | — | — |
| Sulfasalazine | — | — | 10 | — | — | — |
| CaCl2 | — | — | — | — | — | — |
| KH2PO4 | — | — | — | — | — | 1-5 |
| NaCl | — | — | — | — | — | 600-900 |
| MgSO4 * 7H2O | — | — | — | — | — | — |
| KCl | — | — | — | — | — | — |
| NaHCO3 | — | — | — | — | — | — |
| Ciprofloxacin | — | — | — | — | — | — |
| Methylparaben | 30-50 | 30-50 | 30-50 | 30-50 | 30-50 | — |
| Neomycin SO4 | 30-50 | 30-50 | 30-50 | 30-50 | 30-50 | — |
| Chloramphenicol | 12-20 | 12-20 | 12-20 | 12-20 | 12-20 | 12-20 |
| PH | 7.10 ± 0.02 | 7.10 ± 0.02 | 7.10 ± 0.02 | 7.00 ± 0.02 | 7.10 ± 0.02 | 7.20 ± 0.02 |
| Osmolarity | 315 ± 10 | 295 ± 10 | 295 ± 10 | 300 ± 5 | 300 ± 10 | 280 ± 10 |

TABLE 2

TABLE 1

| Chemical | A | | B | | C | | D | | E | | F | | G | |
|---|---|---|---|---|---|---|---|---|---|---|---|---|---|---|
| | mg % | mM | mg % | mM | mg % | mM | mg % | mM | mg % | mM | mg % | mM | mg % | mM |
| EDTA (NA2) | 1675 | 45 | 1173 | 31.5 | 1173 | 31.5 | 704 | 18.9 | 704 | 18.9 | 100 | 2.7 | — | — |
| Mg Gluconate | 933 | 22.5 | 653 | 15.7 | 653 | 15.7 | 392 | 9.45 | 392 | 9.45 | — | — | — | — |
| NA2HPO4 | 639 | 45 | 447 | 31.5 | 447 | 31.5 | 268 | 18.9 | 268 | 18.9 | 73 | 5.1 | 4.9 | 0.34 |
| PEG-20k | 700 | 0.35 | 700 | 0.35 | 700 | 0.35 | 700 | 0.35 | 700 | 0.35 | 1000 | 0.5 | — | — |
| Inosine | 25 | 0.93 | 25 | 0.93 | 25 | 0.93 | 25 | 0.93 | 100 | 3.7 | — | — | — | — |
| Glucose | — | — | 1000 | 55.5 | 1000 | 55.5 | 600 | 33.3 | 600 | 33.3 | — | — | 100 | 5.5 |
| NaF | — | — | 5 | 1.2 | 5 | 1.2 | — | — | — | — | — | — | — | — |
| NaOH | 204 | 51 | 140 | 35 | 140 | 35 | 80 | 20 | 85 | 21.25 | — | — | — | — |
| BSA | — | — | — | — | 2000 | — | — | — | — | — | — | — | — | — |
| Sulfasalazine | — | — | — | — | 10 | 0.25 | — | — | — | — | — | — | — | — |
| CaCl2 | — | — | — | — | — | — | — | — | — | — | — | — | 14 | 1.3 |
| KH2PO4 | — | — | — | — | — | — | — | — | — | — | 2 | 0.15 | 6 | 0.44 |
| NaCl | — | — | — | — | — | — | — | — | — | — | 830 | 142 | 800 | 136.9 |
| MgSO4 * 7H2O | — | — | — | — | — | — | — | — | — | — | — | — | 20.1 | 0.82 |
| KCl | — | — | — | — | — | — | — | — | — | — | — | — | 40 | 5.4 |
| NaHCO3 | — | — | — | — | — | — | — | — | — | — | — | — | 35 | 4.2 |
| Ciprofloxacin | — | — | — | — | — | — | — | — | — | — | — | — | 2 | — |
| Methylparaben | 40 | 2.6 | 40 | 2.6 | 40 | 2.6 | 40 | 2.6 | 40 | 2.6 | — | — | 40 | 2.6 |
| Neomycin SO4 | 40 | 0.44 | 40 | 0.44 | 40 | 0.44 | 40 | 0.44 | 40 | 0.44 | — | — | 40 | 0.44 |
| Chloramphenicol | 15 | 0.46 | 15 | 0.46 | 15 | 0.46 | 15 | 0.46 | 15 | 0.46 | 15 | 0.46 | 15 | 0.46 |
| PH | 7.10 ± 0.02 | | 7.10 ± 0.02 | | 7.10 ± 0.02 | | 7.00 ± 0.02 | | 7.10 ± 0.02 | | 7.20 ± 0.02 | | 7.40 ± 0.20 | |
| Osmolarity | 315 ± 10 | | 295 ± 10 | | 295 ± 10 | | 300 ± 5 | | 300 ± 10 | | 280 ± 10 | | 280 ± 10 | |

What follows is a summary of certain particular approaches for preparing blood cell components (e.g., for providing a blood cell fraction) for use in a cellular fraction for a control in accordance with the present invention. One process includes the steps of providing a source of blood cells; separating and removing unwanted components (e.g., components other than red blood cells). The remaining components are processed to cause them to simulate one or more components of whole blood; and the components are optionally processed (e.g., fixed) for preserving long term stability. Resulting components may then be re-suspended in a desirable suspension medium.

According to another process, there is included a step of processing one or more components to change the size. For example, a component may be processed to expand the cell size relative to its initial size, shrink the cell relative to its initial size, or a combination thereof. Before, during, or even after the step of expanding and/or shrinking a cell it is possible that material may be removed from the cell, added to the cell, altered within the cell or a combination thereof. For example, it is possible that a nucleus, hemoglobin, cytoplasm or other matter may be removed or altered, e.g., in accordance with the teachings of one or more of U.S. Pat. Nos. 6,723,563; 6,653,137; or 5,320,964; all incorporated by reference. An illustration of the addition of a material into a cell is shown in U.S. Pat. No. 5,432,089, hereby incorporated by reference, pursuant to which a blood cell is loaded with a nucleic acid or a polyanion.

The source blood is typically received suspended to include a plurality of cells in a liquid medium, and may include one or more ingredients such as an anticoagulant. Accordingly, it may be desirable to separate the cells from the as-provided liquid medium and to wash the cells. One or more separation steps may be employed, such as centrifugation, filtration or both. Typically, washing will employ contacting the cells with a suitable solution, preferably a buffered solution, and most preferably a suitable isotonic wash solution.

More specifically, the isotonic wash solution will have a pH of at least about 6.0. Still more preferably, the solution will have a pH ranging from about 6.8 to 7.6. Most preferably, the solution will have a pH ranging from 7.0 to 7.2. In a preferred embodiment of the present invention, the osmolarity of the solution will be at least about 270 mOsm. More preferably, the solution will have an osmolarity ranging from about 280 to about 325 mOsm. Most preferably, the solution will have an osmolarity ranging from about 285 to 305 mOsm. One preferred approach is to employ as the substantially isotonic solution, a solution with an osmolarity that is not hypotonic (namely one having an osmolarity substantially below that of ordinary blood plasma).

The wash solution, which generally will be substantially isotonic, may include any of a number of ingredients in a deionized and/or distilled water base. For example, the wash solution may include at least one or more, more preferably two or more, still more preferably three or more, still more preferably four or more and still even more preferably all of the following ingredients: a fungicide; an antimicrobial; a surfactant; a buffer; a metal chelating agent; a cell nutrient; or an agent for maintaining tonicity. For example, in one particular embodiment of the present invention, the relative amounts of the above ingredients may be as follows: a fungicide of up to about 5 parts; an antimicrobial of up to about 5 parts; a surfactant ranging from about 5 parts to about 20 parts; a buffer ranging from about 5 parts to about 30 parts, a metal chelating agent ranging from about 25 parts to 50 parts; a cell nutrient of up to about 5 parts; and an agent for maintaining tonicity in about 15 parts to about 35 parts.

The wash solution may also contain other ingredients as described in U.S. Pat. Nos. 5,858,790 or 6,187,590 (incorporated by reference herein). The isotonic wash solution may also include ingredients that act as a hemolysis inhibitor, an aggregating agent, a cell stabilizer, an antioxidant, or a mixture thereof. By way of example, one possible wash solution may include about 40 mg % Methyl Paraben, about 300 mg % Polyethylene Glycol—(molecular weight about 20,000); about 1675 mg % Ethylenediaminetetraacetic Acid; about 933 mg % Magnesium Gluconate; about 639 mg % Sodium Phosphate Dibasic anhydrous, about 25 mg % Adenosine, about 25 mg % Inosine; about 40 mg % Neomycin Sulfate; and about 15 mg % Chloramphenicol.

In general, unless stated otherwise, initial cell preparation steps (and subsequent processing steps) generally will be performed under conditions that will serve to maintain the structure of the cell nuclei and cell membranes. However, it is possible that a cell may be processed for removing some or all of a nucleus, stripping some or all of a membrane, perforating the membrane, or any combination thereof.

For one or more of the blood cell components useful herein it is possible to avoid any intermediate processing step following the washing step, and to proceed immediately to a stabilization step, such as a fixing step to preserve the structure of the cell for achieving long-term (e.g., at least about 30 days, more preferably at least about 45 days, or at least about 60 days, and possibly even 90 days or longer). In general, the fixing step will include a step of contacting the cell with a suitable concentration of a fixative, a step of heating, or a combination thereof, for a predetermined amount of time. The amount of time required for fixation varies depending on cell concentration, temperature and the strength of the fixative reagent. Various approaches to fixing are illustrated throughout the literature, including in U.S. Pat. Nos. 6,723,563; 6,653,137; 6,221,668; 6,200,500; 5,320,964; all incorporated by reference.

The fixative may include but is not limited to an aldehyde, oxazolidine, alcohol, cyclic urea, or the like. Examples of such fixatives include, without limitation, formaldehyde, glutaraldehyde, diazolidinyl urea (DU), imidazolidinyl urea (IDU), dimethylol urea, dimethylol-5,5-dimethylhydantoin, 2-bromo-2-nitropropane-1,3-diol; quaternary adamantine, hydroxyl-methyl-1-aza-3,7-dioxabicyclo(3.3.0)octane, sodium hydroxymethyl glycinate, and mixtures thereof, or the like. Other fixatives may be used such as those disclosed in U.S. Pat. Nos. 5,196,182; 5,262,327; 5,460,797; 5,811,099; 5,849,517; 6,221,668; 5,529,933; 6,187,590 (incorporated by reference herein). The appropriate fixative reagent is selected based upon the cell attribute to be evaluated by a hematology analyzer. In a preferred embodiment, the present invention utilizes a fixation process to generate the control composition. In one particular embodiment of the present invention, the blood cell fixation begins by contacting the washed blood cells with a fixative reagent. Prior to contacting the blood cells, the fixative may be diluted with water, isotonic solution, hypertonic solution, hypotonic solution or any mixture thereof. The ratio of fixative to diluent ranges from 1:1 to 1:300. More preferably, the ratio of fixative to diluent ranges from 1:1 to 1:100. Most preferably, the ratio of fixative to diluent ranges from 1:3 to 1:50.

In one aspect, for a relatively highly concentrated fixative solution, the fixing preferably takes place for a suitable period of time, such as ranging from about 1 to about 10 hours, more preferably about 3 to about 7 hours and still more preferably about 4 to about 5 hours.

In another embodiment, when the fixative is substantially diluted, the blood cells may be contacted with the diluted fixative reagent for a longer period of time, such as at least about 12 hours. More preferably, the blood cells are contacted with the diluted fixative reagent for a period of time ranging from about 18 hours to about 24 hours. Even more preferably, the blood cells are contacted with the diluted fixative reagent for a period of time ranging from about 18 hours to about 20 hours.

The controls herein are particularly useful as a stand-alone control, such that the control has as its primary objective the simulation of erythroblasts. However, it may be possible that components prepared according to the present teachings will be introduced into a control that also simulates other blood cell components, such as components for simulating a three or five part differential for white blood cells. Examples of commercially available products include the STAK CHEX® product from Streck Laboratories and the 5C™ control from BeckmanCoulter. The controls may be employed with components for other blood cell components as discussed herein and/or three or five part white blood cell differentials.

The fixation may take place at room temperature or at a temperature below room temperature or at a temperature above room temperature. If the fixation takes place below room temperature, the cooling is set to at least about 15° C. More preferably the fixation will take place at a temperature in the range of 15° C. to 0° C. Even more preferably, the fixation will take place at a temperature in the range of 10° C. to 5° C. Most preferably the fixation will take place at 6° C. If the fixation takes place above room temperature, the heating is set to at least about 30° C. More preferably the fixation will take place at a temperature in the range of 30° C. to 50° C. Even more preferably, the fixation will take place at a temperature in the range of 35° C. to 40° C. Most preferably the fixation will take place at 40° C.

The fixative may also be combined with one or more other ingredients prior to or during the step of contacting the fixative with the washed blood cells. For example, one or more of a sugar, alcohol, another hydroxyl containing agent or any combination thereof may be employed. By way of example, it is possible to include an agent such as sorbitol (e.g., in an amount of about 0.5 to about 5% by weight).

It is also possible that a step of contacting with a fixative may be omitted. For example, in one such approach, the cells are provided from their respective source. They are washed with an isotonic wash solution in one or more washing steps. In one preferred embodiment, they are kept in such a solution while being maintained at a temperature of about 10 to about 40° C., and more preferably about 18 to about 30° C. for longer than about one hour, more preferably longer than about 3 hours and still more preferably longer than about 12 hours (e.g., about 22 to about 30 hours).

If employed, any step of shrinking or swelling may be done by one or more techniques. For example, one approach includes a step of swelling a cell in a hypotonic solution (e.g., having an osmolarity of lower than 300 mOsm). Another approach includes a step of swelling a cell in a hypertonic solution (e.g., having an osmolarity of greater than 300 mOsm).

In a preferred embodiment of the present invention, the fixed blood cells are washed out of the fixative reagent and resuspended into a suitable suspension medium. The cells can be washed out of the fixative reagent with a buffered isotonic solution.

The following discusses examples of methods of using the control composition to determine the accuracy and reproducibility of the operation of a multi-parameter automated hematology instrument. By way of example, a multi-parameter automated hematology instrument, such as a Beckman Coulter Gen-S or LH-Series Systems (e.g., LH-700 System (optionally employing ACCUCOUNT technology offered by BeckmanCoulter)), the Abbott Cell-Dyn 4000 Hematology System, Bayer ADVIA 120, and the Sysmex XE2100 System, is provided, optionally with a slide preparation module. The claimed control composition is obtained or prepared, optionally to illustrate low, normal or high values of a blood cell component. The control optionally is refrigerated prior to use. If so, at the beginning of testing, the control composition is allowed to warm to room temperature for about fifteen minutes, mixed manually, and checked for re-suspension of contents.

In one embodiment, it is desirable for at least one of the detectable cellular components resulting from the processing steps herein have characteristics that would resemble that of a normal human erythroblast. For example, it may have an overall average cell size ranging from about 100 to about 650 fl, more specifically about 400 to about 600 fl (e.g., about 425 to about 575 fl). Desirably such cellular component will include a nucleus. But, it is possible that a nucleus will be at least partially, if not fully excluded from the cell.

The control composition is prepared and analyzed by the same standard method as test samples which may be tested in batch quantities by the use of a suitable cassette having apertures for receiving test vials. After preparation, the control composition and test samples are analyzed by detecting the presence of or counting the population number of each subject component type with a multi-parameter automated hematology instrument, which will preferably yield a visual display of the data. In one embodiment the control of the present invention is provided in combination with a peripheral device, such as a device for tracking samples and associating them with particular data, e.g., a bar-code scanner system, an RFID system or otherwise. The control may also be provided in combination with a slide preparation kit, stain or dye-resistant labels, lytic reagents (e.g., containing a quaternary ammonium salt), blood diluents, or other like components used in a clinical laboratory setting.

The automated test instrument may employ technology that analyzes cell samples in view of simultaneous volume conductivity and light scatter measurements, or solely by light scatter. Ordinarily, a starting sample is employed in combination with suitable reagents (which may comprise a component of a kit) and physical agitation for lysing and cell measuring by way of flow cytometry.

Examples of the various analysis techniques that might be employed will be apparent by familiarity with the above identified commercially available instruments, as well as by reference to art-disclosed techniques discussed in U.S. Pat. No. 6,060,322 (discussing "mixing a blood cell sample containing reticulated cells with a reagent composition comprising a metachromatic dye and a sphering agent to form a suspension of cells; U.S. Pat. No. 6,232,125 (stating that "Light scattering characteristics of the leukocytes are determined within five different angular ranges, all being lower than 40 degrees"); U.S. Pat. No. 6,228,652 (discussing use of "single transducer for simultaneously measuring the DC volume, RF conductivity, light scattering and fluorescence characteristics of blood cells passing through a cell-interrogation zone"); U.S. Pat. No. 5,917,584 (discussing "differentiation and enumeration of nucleated red blood cells without using fluorescence"); U.S. Pat. No. 5,874,311 (discussing "measuring low angle light scatter signal detected in less than 10° to differentiate reticulocytes from other cell types") U.S. Pat. No. 5,874,310 (discusses "exposing a blood cell sample to a reagent system to lyse mature red blood cells and subsequently analyzing nucleated red blood cells in a flow cell by optical analysis" and the use of "two angles of light scatter signals" such as "low angle light scatter signals detected in less than 10°"). Other techniques are also discussed in U.S. Pat. Nos. 5,858,790 and 6,187,590. Of course, by no means is the mode of sample testing limited to the above. As mentioned other principles may be used. One preferred approach is to employ the controls of the present invention in a process (e.g., by passing the control through a suitable instrument) by which erythroblasts are differentiated from other cell types using axial light loss and low angle light scatter measurements, (e.g., from about 1° to 9°, and more specifically from about 3° to 7°), axial light loss and DC impedance measurements, or any combination thereof.

Thus, in one embodiment, the present invention contemplates a method of using a control including an erythroblast simulation component including the steps of providing a control including at least one stabilized blood cell component suitable for simulating an erythroblast. The control (which may be provided in a kit) may also have other components such as those described herein, such as a white blood cell component for simulating at least five subpopulations of white blood cells. In one preferred embodiment, though not required, the white blood cell component has been prepared from a red blood cell, a white blood cell, or a mixture thereof, at least one of which has been contacted with a lipoprotein.

A hematology analyzer is provided. Preferably the analyzer is also adapted for differentiating white blood cells and for analyzing a blood cell sample by light scatter (e.g., by measuring low angle light scatter signals), and more preferably by two angles of light scatter measurement, which may include a medium angle light scatter signal and a right-angle light scatter. Preferably both signals (or only one if a single angle scatter is used) are less than about 10° (e.g., from about 1 to about 7°, or for some multi-angle scatter measurements, one light scatter angle may be in the range of about 0 to about 4° and the other light scatter angle is in the range of about 3 to about 7°) to differentiate erythroblasts from other cell types. The control is passed through the hematology analyzer at a suitable temperature (e.g., at a temperature in the range of about 18 to about 28° C., though higher or lower temperatures are also possible). It is possible that the analyzer detects cells by measuring axial light loss signals and DC impedance. The analyzer may detect cells by measuring low angle light scatter signals in combination with measuring axial light loss signals and DC impedance. Optionally, the detection of the simulated erythroblast is performed in the absence of a fluorescent stain or dye. In one embodiment, the control is passed though the instrument only a single time, in order to obtain a satisfactory result. In another embodiment, the control is repeatedly passed though the instrument to assure test integrity.

The results of the analysis, which will resemble that of whole blood, may then be analyzed and reported. For example, the respective population counts obtained from the analysis are compared either to known reference value for each component type in the control composition, or by comparison of the population counts for each component types in the test sample with the corresponding values of components in the control composition. Data relating to the measurement of components in control composition and test samples is collected, monitored, stored, compared and analyzed by electronic means, such as part of a system including a computer programmed with appropriate software and containing appropriate data file structure, and preferably coupled with one or more devices for outputting or storing the data (e.g., a monitor, a printer, an electronic data storage medium or the like).

By way of summary of the above teachings, and with reference to the examples herein, the present invention is directed to cellular fractions, controls that employ cellular fractions, as well as the methods for making the cellular fractions and the controls.

Though disclosed herein in the context of a control composition, in one aspect, the present invention pertains to a cellular fraction for a blood cell control (e.g., a stand-alone erythroblast control), which includes or consists essentially of a first cellular component including a plurality of a first group of processed animal red blood cells other than human blood cells; a second cellular component including a plurality of a second group of processed animal red blood cells other than human blood cells; and a third cellular component including a plurality of a third group of processed animal red blood cells other than human blood cells; wherein one or more of the first, second and third cellular components include a nucleus; and at least a portion of the cellular fraction functions to simulate erythroblasts of a human blood sample on an automated blood analyzer that analyzes blood cells using impedance, optical measurements or both.

The cellular fractions may include cells that have been derived from one or more of the first, second or third cellular components is a processed red blood cell derived from alligators, turkeys, geese, chickens, sharks, cows, pigs, goats, salmon, trout, or another source of a blood cell with a nucleus. At least one of the first, second or third cellular components is a processed red blood cell derived from alligators. The fractions may also include a lysable red blood cell component.

Cells from the third cellular component of the cellular fraction will function to simulate erythroblasts of a human blood sample on an automated blood analyzer that analyzes blood cells using impedance, optical measurements or both. Further it is possible that upon passing through an automated hematology analyzer cells of the first and second cellular components are detected by the analyzer as a white blood cell, and cells of the third cellular component are detected as an erythroblast. It is further possible that, upon analysis of the cells by the analyzer, the cells of the cellular components (and particularly the first and second components) fail to provide a white blood cell differentiation (e.g., a three subpopulation differential, a five subpopulation differential or both) within ranges consistent with normal human whole blood (e.g., within the ranges of about Lymphocytes—20 to 45%; Monocytes—2 to 10%; Neutrophils—40 to 75%; Eosinophils—1 to 6%; and Basophils up to 1%).

The invention also can be regarded as a hematology control (whether a stand-alone control or not), which includes a first part that includes a plurality of cellular components; and a second part that includes at least one cellular component including a plurality of alligator red blood cells processed for simulating erythroblasts of a human blood sample on an automated blood analyzer; wherein upon passing through an automated hematology analyzer the cellular components of the first part are detected by the analyzer as a white blood cell, and the second part is detected as an erythroblast. In such instance, any of the above described sources of blood cells may be employed. However, desirably, the cellular component of the second part includes red blood cells derived from an alligator. As with the above, the cellular components of the first part, upon analysis by the analyzer fail to provide a white blood cell differentiation (e.g., a three subpopulation differential, a five subpopulation differential or both) within ranges consistent with normal human whole blood (e.g., within the ranges of about Lymphocytes—20 to 45%; Monocytes—2 to 10%; Neutrophils—40 to 75%; Eosinophils—1 to 6%; and Basophils up to 1%). In the latter aspect, at least a portion of the second part functions to simulate erythroblasts of a human blood sample on an automated blood analyzer that analyzes blood cells using impedance, optical measurements or both.

As will be seen, in certain respects, the invention also pertains to a method of making a control for resembling an erythroblast population, comprising the steps of admixing in an aqueous diluent: a first cellular component (as described above) including a plurality of a first group of processed animal red blood cells other than human blood cells; a second cellular component (as described above) including a plurality of a second group of processed animal red blood cells other than human blood cells; and a third cellular component (as described above) including a plurality of a third group of processed animal red blood cells other than human blood cells; wherein one or more of the first second and third cellular components include a nucleus; and the resulting control simulates erythroblasts of a human blood sample on an automated blood analyzer that analyzes blood cells using impedance, optical measurements or both.

It may also include steps of admixing in an aqueous diluent a first part that includes a plurality of cellular components; and a second part that includes at least one cellular component including a plurality of alligator red blood cells processed for simulating erythroblasts of a human blood sample on an automated blood analyzer; wherein upon passing through an automated hematology analyzer the cellular components of the first part are detected by the analyzer as a white blood cell, and the second part is detected as an erythroblast.

The skilled artisan will appreciate that a number of the steps and ingredients have been disclosed by way of example, but that any of a number of alternative steps or ingredients at the suggested or different parameter or concentration, may be suitably substituted. Though the ingredients or steps have been, in certain instances, described by reference to a particular function or result, it should be appreciated that such discussion is presented without intending to be bound by theory. In some instances, the ingredient or step will perform a different or an additional function or achieve a different result, or multiple other ingredients or steps may be substituted to perform such function or achieve such result. Thus, there is no intention to be bound to the breadth of any specific illustrative step, parameter, ingredient or concentration, where it is apparent that others may be advantageously be employed in addition to or as a substitute.

The present invention is further illustrated by particular reference to the following examples, it being understood that variations of the same may be made while still remaining within the scope of the invention. In the examples that follow, as well as in accordance with the preceding teachings (to which the discussion in this paragraph also applies), it is expected that the resulting cellular components will be capable of detection by an automated hematology analyzer. The resulting sizes of the cellular components may be substantially the same as the starting cells, larger or smaller. When different, the cellular components may range from about one half to about twice the size of the original cells. In certain instances, it is also possible that hemoglobin may be removed from within the cell, with removals (when occurring) ranging from about 0% to about 100% of the original hemoglobin (e.g., less than about 10%, less than about 20%, greater than about 70%, greater than about 85% or otherwise).

EXAMPLE 1

Alligator red blood cells are selected having a mean cell volume range of 230-320 fl. The cells are washed with a solution such as Solution A of Table 1 or 2, and centrifuged three times at 1000 rpm for 10 minutes. Cells are diluted in Solution A of Table 1 or 2 to a concentration of $0.1 \times 10^6$/ul. A fixative reagent is prepared, having a glutaraldehyde concentration of about 0.05% in Solution A. The washed red blood cells are then added to the fixative reagent. The preparation is then incubated (e.g., sealed and rolled slowly) for 18 to 24 hours at room temperature. Supernatant is removed and the cells are washed with a solution such as Solution A of Table 1 or 2, and centrifugated three times at 1000 rpm for 10 minutes. The resulting cell component is resuspended in a solution such as Solution A of Table 1 or 2.

EXAMPLE 2

Alligator red blood cells are selected having a mean cell volume range of 230-320 fl. The cells are washed with a phosphate buffered saline solution, and centrifuged three times at 1000 rpm for 10 minutes. A fixative reagent is prepared, having a glutaraldehyde concentration of about 0.3% by adding to the Solution A of Table 1 or 2. The washed red blood cells are then added to the fixative reagent. The washed red blood cells are contacted with the fixative reagent. The preparation is then incubated (e.g., sealed and rolled slowly) for 18 to 24 hours at room temperature. Supernatant is removed and the cells are washed with a solution such as Solution A of Table 1 or 2, and centrifuged three times at 1000 rpm for 10 minutes. The resulting cell component is re-suspended in a solution such as Solution A of Table 1 or 2.

EXAMPLE 3

Alligator red blood cells are selected having a mean cell volume range of 230-320 fl. The cells are washed with a phosphate buffered saline solution, and centrifuged three times at 1000 rpm for 10 minutes. A fixative reagent is prepared, having a glutaraldehyde concentration of about 0.05% in a phosphate buffered saline solution in a 1:1 ratio. The washed red blood cells are contacted with the fixative reagent. The preparation is then incubated (e.g., sealed and rolled slowly) for 18 to 24 hours at room temperature. Cell count is adjusted to 50,000 (e.g., to reflect a concentration of simulated erythroblasts) and the cells are contacted in 1:5 parts with 30% alcohol solution (methyl, isopropyl, ethyl or a combination thereof) in phosphate buffered saline solution for 18-24 hours at room temperature, and thereafter re-suspended in phosphate buffered saline solution.

EXAMPLE 4

Alligator red blood cells are selected having a mean cell volume range of 230-320 fl. The cells are washed with a solution such as Solution A of Table 1 or 2, and centrifuged three times at 1000 rpm for 10 minutes. Cells are diluted in Solution A to Table 1 or 2 to a concentration of $0.1 \times 10^6$/ul. A fixative reagent is prepared, having a glutaraldehyde concentration of about 0.0125% in a hypertonic water solution containing about 3% dimethyl sulfoxide. The washed red blood cells are contacted with the fixative reagent. The preparation is then incubated (e.g., sealed and rolled slowly) for 18 to 24 hours at room temperature. Cell count is adjusted to 50,000 (e.g., to reflect a concentration of simulated erythroblasts) and the cells are contacted in 1:5 parts with 30% alcohol solution (methyl, isopropyl, ethyl or a combination thereof) in phosphate buffered saline solution for 18-24 hours at room temperature. Supernatant is removed, and cells centrifuged three times at 1000 rpm for 10 minutes, in a phosphate buffered saline solution also including surfactant (e.g., 0.1% Triton X surfactant).

EXAMPLE 5

Alligator red blood cells are selected having a mean cell volume range of 230-320 fl. The cells are washed with a solution such as Solution A of Table 1 or 2, and centrifuged three times at 1000 rpm for 10 minutes. Cells are diluted in Solution A of Table 1 or 2 to a concentration of $0.1 \times 10^6$/ul. A fixative reagent is prepared, having a glutaraldehyde content of about 0.075% in a hypertonic water solution containing about 3% dimethyl sulfoxide. The washed red blood cells are contacted with the fixative reagent. The preparation is then incubated (e.g., sealed and rolled slowly) for 18 to 24 hours at room temperature. Supernatant is removed and the cells are washed with a solution such as Solution A of Table 1 or 2, and centrifuged three times at 1000 rpm for 10 minutes. The resulting cell component is re-suspended in a solution such as Solution A of Table 1 or 2.

EXAMPLE 6

Alligator red blood cells are selected having a mean cell volume range of 230-320 fl. The cells are washed with a solution such as Solution A of Table 1 or 2, and centrifuged three times at 1000 rpm for 10 minutes. Cells are diluted in Solution A to Table 1 or 2 to a concentration of $0.1 \times 10^6$/ul. A fixative reagent is prepared, having a glutaraldehyde concentration of about 0.0125% in Solution A to Table 1 or 2. The washed red blood cells are contacted with the fixative reagent. The preparation is then incubated (e.g., sealed and rolled slowly) for 18 to 24 hours at room temperature. Supernatant is removed and the cells are washed with a solution such as Solution A of Table 1 or 2, and centrifuged three times at 1000 rpm for 10 minutes. The resulting cell component is re-suspended in a solution such as Solution A to Table 1 or 2.

EXAMPLE 7

The process of Example 6 is performed, except that the solution D of Table 1 or 2 is substituted for the Solution A throughout the process. Additionally, instead of glutaraldehyde, there is employed a fixative of about 4% diazolidinyl urea.

EXAMPLE 8

The cells of Examples 1-7 are combined together in different combinations and analyzed on either a Coulter LH-750 instrument or a Bayer Advia instrument. The analyzer detects the presence of erythroblasts at the expected level. In particular, 500 ml of lysable human red blood cells are combined with 2 ml of resulting cellular components from Example 4, 18 ml of resulting cellular components from Example 5 and 2 ml of resulting cellular components of Example 6 and diluted in 479 ml Solution C of Table 1 or 2.

EXAMPLE 9

This example illustrates a control in which all of the cellular components are derived from alligator red blood cells.

A first cellular component is made by washing alligator red blood cells, centrifugating and then re-suspending them in the Solution A of Table 1 or 2 so the final cell suspension contains 100,000 RBC per µl. A fixative solution is prepared by adding glutaraldehyde Solution A of Table 1 or 2 to a concentration of 0.025% (w/v). One part of cell suspension is mixed with 1 part of fixative solution. The RBC count in fixing solution is 50,000/µl and the glutaraldehyde concentration is 0.0125% (w/v). Fixation continues for 18 to 24 hours. Cells are then washed from fixing solution into the Solution A of Table 1 or 2. Storage concentration is about 100,000 cells/µl.

A second cellular component is made by washing alligator red blood cells, centrifugating and then re-suspending them in the Solution A of Table 1 or 2, so the resulting suspension contains 500,000 red blood cells per µl. A water fixative solution is prepared by adding glutaraldehyde to water to a concentration of 0.1% (w/v). One part of cell suspension is mixed with 100 parts of water fixative solution. The diluted red blood cell count is then 5,000/μl and glutaraldehyde concentration is about 0.1% (w/v). Fixation continues for 18 to 24 hours. Cells are then washed into a phosphate buffered saline wash solution containing 0.1% Triton X 705, 73 mg % sodium phosphate dibasic, 900 mg % sodium chloride, 2 mg % potassium phosphate and 3.3 ml/l Proclin 300. Isopropyl alcohol is added to the wash solution to a concentration of 30% (w/v). The cells are then separated and re-suspended in the phosphate buffered saline wash solution. Storage concentration is about 100,000 cells/μl.

A third cellular component is made by washing alligator red blood cells, centrifugating and then re-suspending them in the Solution A of Table 1 or 2, so that the resulting suspension contains 100,000 RBC per μl. A fixative solution is prepared by adding glutaraldehyde to NaCl solution (100 msoM) to a concentration of 0.05%. One part of cell suspension is mixed with 50 parts of fix solution so that the red blood cell count in the fixing solution is 2,000/μl and the glutaraldehyde concentration is about 0.05%. Fixation continues for 18 to 24 hours. Cells are then washed into the Solution A of Table 1 or 2. Storage concentration is about 200,000 cells/μl.

A stand-alone control is prepared by mixing about two parts of the first cellular component, about two parts of the second cellular component, and about 9 parts of the third cellular component into Solution C of Table 1 or 2 in the following concentrations: first cellular component (about 100 to 200 cells/μl); second cellular component (about 200 cells/μl); and third cellular component (about 1800 cells/μl).

A stabilized human red blood cell component is also included to provide a concentration of about 3 million cells/μl. As with the controls taught generally herein, when analyzed in an automated hematology analyzer (e.g., a Coulter LH 750 or 780 series analyzer), the control results in the identification and enumeration of cells of one or more of the cellular components as nucleated red blood cells, particularly without manual intervention.

It will be appreciated that concentrates or dilutions of the amounts recited herein may be employed. In general, the relative proportions of the ingredients recited will remain the same. Thus, by way of example, if the teachings call for 30 parts by weight of a Component A, and 10 parts by weight of a Component B, the skilled artisan will recognize that such teachings also constitute a teaching of the use of Component A and Component B in a relative ratio of 3:1.

It will be appreciated that the above is by way of illustration only. Other ingredients may be employed in any of the compositions disclosed herein, as desired, to achieve the desired resulting characteristics. Examples of other ingredients that may be employed include antibiotics, anesthetics, antihistamines, preservatives, surfactants, antioxidants, unconjugated bile acids, mold inhibitors, nucleic acids, pH adjusters, osmolarity adjusters, or any combination thereof. Specific examples of ingredients that may be employed include one or more of sodium fluoride, a paraben (e.g., propyl), sulfasalazine, soybean protease inhibitor, sodium phosphate, potassium phosphate, sodium citrate, citric acid, sodium chloride, bovine serum albumin, sodium hydroxide, lipoprotein, Proclin, adenine, mannose, dextrose, lactose, penicillin, tetracycline, promethazine, a purine (e.g., adenine), inosine, kanamycin sulfate, cyclohexamide, deoxycholic acid, colistimethate sodium, trisodium citrate dehydrate, 5-Fluorouracil, or any combination thereof.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A method of making a stand-alone control for resembling an erythroblast population, comprising the steps of admixing in an aqueous diluent:
   a first cellular component including a plurality of a first group of processed animal red blood cells other than human blood cells;
   a second cellular component including a plurality of a second group of processed animal red blood cells other than human blood cells; and
   a third cellular component including a plurality of a third group of processed animal red blood cells other than human blood cells;
   wherein one or more of the first, second and third cellular components are composed of alligator red blood cells that have been fixed and swollen using a hypertonic solution and upon passing through an automated hematology analyzer the cellular components of at least one of the first, second and third cellular components are detected by the analyzer as white blood cells but fail to provide a white blood cell differentiation within ranges consistent with human whole blood, and at least one of the first, second and third cellular components is detected as an erythroblast on an automated blood analyzer that analyzes blood cells using impedance, optical measurements or both.

2. The method of claim 1, wherein one or more of the first, second or third cellular components other than the one or more cellular components composed of alligator red blood cells is a processed red blood cell derived from, turkeys, geese, chickens, sharks, cows, pigs, goats, salmon, trout, or another source of a blood cell with a nucleus.

3. The method of claim 2, wherein the third cellular component is a processed red blood cell derived from alligators.

4. The method of claim 1, wherein cells from the third cellular component function to simulate erythroblasts of a human blood sample on an automated blood analyzer that analyzes blood cells using impedance, optical measurements or both.

5. The method of claim 4, wherein upon passing through an automated hematology analyzer cells of the first and second cellular components are detected by the analyzer as a white blood cell, and cells of the third cellular component are detected as an erythroblast.

6. The method of claim 4, wherein the third cellular component has a size prior to processing from about 160 fL to about 330 fL.

7. The method of claim 1, wherein the alligator red blood cells are simultaneously fixed and swollen.

8. The method of claim 7, wherein the alligator red blood cells are simultaneously fixed and swollen by contact with a solution containing gluteraldehyde and dimethyl sulfoxide.

9. The method of claim 1, wherein the method further comprises a step of cross-linking or otherwise denaturing a cell membrane of the processed animal red cells.

10. A cellular fraction for a stand-alone erythroblast control, comprising:
    a first cellular component including a plurality of a first group of processed animal red blood cells other than human blood cells;
    a second cellular component including a plurality of a second group of processed animal red blood cells other than human blood cells; and
    a third cellular component including a plurality of a third group of processed animal red blood cells other than human blood cells;
    wherein one or more of the first, second and third cellular components include a nucleus and are composed of alligator red blood cells that have been fixed and swollen using a hypertonic solution and upon passing through an automated hematology analyzer the cellular components of at least one of the first, second and third cellular components are detected by the analyzer as white blood cells but fail to provide a white blood cell differentiation within ranges consistent with human whole blood, and at least one of the first, second and third cellular components is detected as an erythroblast on an automated blood analyzer that analyzes blood cells using impedance, optical measurements or both.

11. The cellular fraction of claim 10, wherein upon passing through an automated hematology analyzer cells of the first and second cellular components are detected by the analyzer as a white blood cell, and cells of the third cellular component are detected as an erythroblast.

12. The cellular fraction of claim 11, wherein the third cellular component has a size prior to processing from about 160 fL to about 330 fL.

13. The cellular fraction of claim 10, wherein the alligator red blood cells are simultaneously fixed and swollen by contact with a solution containing gluteraldehyde and dimethyl sulfoxide.

14. The cellular fraction of claim 10, wherein the cellular fraction includes about two parts of the first component, about two parts of the second component, and about 9 parts of the third component.

15. The cellular fraction of claim 14, wherein the cellular fraction includes about 100 to about 200 cells/µl of the first component, about 100 to about 200 cells/µl of the second component, and about 1600 to about 1900 cells/µl of the third component.

16. The cellular fraction of claim 10, wherein one or more of the first, second, and third group of processed animal red blood cells include a membrane that has been cross-linked or otherwise denatured.

17. The cellular fraction of claim 10, wherein one or more of the first, second or third cellular components other than the one or more cellular components of alligator red blood cells is a processed red blood cell derived from, turkeys, geese, chickens, sharks, cows, pigs, goats, salmon, trout, or another source of a blood cell with a nucleus.

18. A cellular fraction for a stand-alone erythroblast control, consisting essentially of:
    a lysable cellular cell component for simulating human red blood cells;
    a first cellular component including a plurality of a first group of processed animal red blood cells other than human blood cells;
    a second cellular component including a plurality of a second group of processed animal red blood cells other than human blood cells; and
    a third cellular component including a plurality of a third group of processed animal red blood cells other than human blood cells; tk
    wherein one or more of the first, second and third cellular components include a nucleus and at least a portion of the cellular fraction includes swollen alligator red blood cells that function to simulate erythroblasts of a human blood sample on an automated blood analyzer that analyzes blood cells using impedance, optical measurements or both.

19. The cellular fraction of 18, wherein the cells of the first and second cellular components, upon analysis of the cells by the analyzer fail to provide a white blood cell differentiation within ranges consistent with human whole blood.

20. The cellular fraction of claim 18, wherein one or more of the first, second, and third group of processed animal red blood cells include a membrane that has been cross-linked or otherwise denatured.

21. The cellular fraction of claim 18, wherein the cell membrane of the swollen alligator red blood cells has been cross-linked or otherwise denatured.

22. A cellular fraction for a stand-alone blood cell control, comprising:
    a first part that includes a plurality of cellular components; and
    a second part that includes at least one cellular component including a plurality of swollen alligator red blood cells processed for simulating erythroblasts of a human blood sample on an automated blood analyzer;
    wherein upon passing through an automated hematology analyzer the cellular components of the first part are detected by the analyzer as a white blood cell but fail to provide a white blood cell differentiation within ranges consistent with human whole blood, and the second part is detected as an erythroblast on an automated blood analyzer that analyzes blood cells using impedance, optical measurements or both.

23. The cellular fraction of claim 22, wherein the plurality of alligator red blood cells have been processed in a hypertonic solution for increasing their volume relative to their original cell volume.

24. The cellular fraction of claim 22, wherein the alligator red blood cells are simultaneously fixed and swollen by contact with a solution containing gluteraldehyde and dimethyl sulfoxide.

25. The cellular fraction of claim 22, wherein the cellular component detected as an erythroblast is present in an amount of about 1 to about 15% of the total cells.

26. The cellular fraction of claim 22, wherein the first part includes cells that are processed red blood cell derived from alligators, turkeys, geese, chickens, sharks, cows, pigs, goats, salmon, trout, or another source of a blood cell with a nucleus.

* * * * *